(12) United States Patent
Szita et al.

(10) Patent No.: US 11,033,897 B2
(45) Date of Patent: Jun. 15, 2021

(54) MICROFLUIDIC DEVICE

(71) Applicant: UCL BUSINESS PLC, London (GB)

(72) Inventors: Nicolas Szita, London (GB); Marcel Reichen, London (GB)

(*) Notice: Subject to any disclaimer, the term of this patent is extended or adjusted under 35 U.S.C. 154(b) by 0 days.

(21) Appl. No.: 14/705,309

(22) Filed: May 6, 2015

(65) Prior Publication Data

US 2015/0231634 A1 Aug. 20, 2015

Related U.S. Application Data

(63) Continuation of application No. 13/116,577, filed on May 26, 2011, now abandoned, which is a continuation-in-part of application No. PCT/GB2009/002778, filed on Nov. 26, 2009.

(30) Foreign Application Priority Data

Nov. 26, 2008 (GB) .................................... 0821636

(51) Int. Cl.
*C12M 3/06* (2006.01)
*B01L 3/00* (2006.01)
*C12M 1/00* (2006.01)

(52) U.S. Cl.
CPC ....... *B01L 3/502715* (2013.01); *C12M 23/16* (2013.01); *C12M 23/26* (2013.01); *C12M 29/10* (2013.01); *B01L 2200/025* (2013.01); *B01L 2200/027* (2013.01); *B01L 2200/0689* (2013.01); *B01L 2300/0627* (2013.01); *B01L 2300/0816* (2013.01); *B01L 2300/0874* (2013.01); *B01L 2300/10* (2013.01); *B01L 2300/12* (2013.01); *B01L 2400/086* (2013.01); *Y10T 409/303752* (2015.01)

(58) Field of Classification Search
CPC .......................... B01L 2200/027; C12M 23/16
See application file for complete search history.

(56) References Cited

U.S. PATENT DOCUMENTS

| 6,193,647 | B1 * | 2/2001 | Beebe | A61B 17/435 |
| | | | | 600/33 |
| 6,209,928 | B1 | 4/2001 | Benett et al. | |
| 6,319,476 | B1 * | 11/2001 | Victor, Jr. | F15C 5/00 |
| | | | | 210/198.2 |

(Continued)

FOREIGN PATENT DOCUMENTS

| EP | 1 880 765 | 1/2008 |
| JP | 2003-227780 | 8/2003 |

(Continued)

*Primary Examiner* — Jonathan M Hurst
(74) *Attorney, Agent, or Firm* — Miles & Stockbridge P.C.; Ajay Jagtiani

(57) ABSTRACT

The invention relates to a microfluidic device including a chamber having a fluid inlet, a fluid outlet and a sealable port. In some embodiments, the fluid inlet and the fluid outlet may be positioned to direct fluid flowing from the fluid inlet to the fluid outlet through the chamber. Various embodiments may include a sealable port which may be aligned with the chamber to allow material to be placed directly into, or removed from, the chamber from the exterior of the device when the sealable port is open, and to inhibit and/or prevent fluid escaping through the sealable port when the port is sealed.

18 Claims, 7 Drawing Sheets

(56) References Cited

U.S. PATENT DOCUMENTS

| | | | | |
|---|---|---|---|---|
| 6,645,432 B1 * | 11/2003 | Anderson | ............. | B01L 3/0262 |
| | | | | 137/827 |
| 2004/0077075 A1 | 4/2004 | Jensen et al. | | |
| 2005/0089993 A1 | 4/2005 | Boccazzi et al. | | |
| 2006/0199260 A1 | 9/2006 | Zhang et al. | | |
| 2008/0057561 A1 * | 3/2008 | Takahashi | .............. | C12M 23/12 |
| | | | | 435/243 |
| 2010/0009335 A1 * | 1/2010 | Joseph | ................... | C12M 23/12 |
| | | | | 435/3 |

FOREIGN PATENT DOCUMENTS

| | | |
|---|---|---|
| JP | 2004-000163 | 1/2004 |
| WO | 01/09598 | 2/2001 |
| WO | 01/88087 | 11/2001 |
| WO | 20051023124 | 3/2005 |

* cited by examiner

MICROFLUIDIC DEVICE

RELATED APPLICATIONS AND INCORPORATION BY REFERENCE

This application is a continuation of U.S. application Ser. No. 13/116,577 filed May 26, 2011, which is a continuation-in-part application of international patent application Serial No. PCT/GB2009/002778 filed Nov. 26, 2009, which published as PCT Publication No. WO/2010/061201 on Jun. 3, 2010, which claims benefit of GB patent application Serial No. 0821636.8 filed Nov. 26, 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to analytical devices and, in particular, relates to microfluidic devices such as bioreactors used for cell culture.

BACKGROUND OF THE INVENTION

Miniaturised total analysis systems ("µTAS") were proposed as a novel concept for chemical sensing in 1990 [1], creating the field of microfluidics and leading to the vision of lab-on-a-chip. µTAS integrates all steps required in chemical analysis—sampling, pre-processing, and measurement, etc.—into a single device via miniaturisation, resulting in improved selectivity and detection limit compared to conventional sensors [1]. A significant amount of research has been devoted to the development of microfluidics technology and applications of µTAS devices over the past decade [2-5]. Common analytical assays, including polymerase chain reaction (PCR) [6-9], DNA analyses and sequencing [10-13], protein separations [14-18], immunoassay [19-24], and intra- and inter-cellular analysis [25-29] have been reduced in size and fabricated in a centimetre-scale chip. The reduction in the size of the analytical processes has many advantages including rapid analysis, less sample amount, and smaller size [1-5]. The flushing of cells can also potentially lead to unwanted dissociation of cell colonies.

Although there have been many successes, an important hurdle that still needs to be cleared is the connection between the micro-components of a device and the macro-environment of the world. This part of the device is often referred to as the macro-to-micro interface [30], interconnect [31-34], or world-to-chip interface [35-39]. The difficulty results from the fact that samples and reagents are typically transferred in quantities of microlitres (µL) to millilitres (or even litres) whereas microfluidic devices consume only nanolitres (nL) or picolitres of samples/reagents due to the size of reaction chambers and channels, which typically have dimensions on the order of microns. This problem must be overcome for microfluidic devices to be successful, especially for high-throughput applications where manual manipulation is not economical and the macro-to-micro interface must be developed.

Microfluidic devices have also been developed for use in a broad range of cell biology applications [40]. Generally, in these devices a constant perfusion system is used to provide the cells with an adequate supply of medium in order to provide the required nutrient requirements and oxygen supply to keep the cells healthy [41]. However, the problem with using a constant perfusion or flow of medium across the cells is that the cells can be exposed to high shear stress which can be detrimental to the normal functioning of the cells. This is especially the case for highly sensitive cells such as human embryonic stem cells (hESC). Further, if high flow rates are used for the perfusion, cells may be washed out of the microfluidic device by the medium.

Another problem associated with existing microfluidic devices used in cell culture is that it is often difficult to accurately and carefully introduce cells into the cell culture chamber of the microfluidic device. For example, some devices flush the cells into the microfluidic chamber from upstream inlets. This leads to an undefined number of cells in the chamber. The flushing of cells can also potentially affect the phenotype of the cells as a result of exposure to high shear stress.

Citation or identification of any document in this application is not an admission that such document is available as prior art to the present invention.

SUMMARY OF THE INVENTION

The present invention provides a microfluidic device which may include a chamber having a fluid inlet, a fluid outlet and a sealable port. In some embodiments, the fluid inlet and the fluid outlet may be positioned to direct fluid flowing from the fluid inlet to the fluid outlet through the chamber. The sealable port may be aligned with the chamber to allow insertion of material into the chamber or extraction of material from the chamber when the sealable port is open, and to inhibit and/or prevent fluid from escaping through the sealable port when the port is sealed.

In some embodiments, a microfluidic device may include an interconnect system having a first component which includes a conduit to carry fluid to the fluid inlet or away from the fluid outlet. Some embodiments may include a first component formed of a deformable material. Some embodiments of a microfluidic device may include a second component having a projecting portion. In some embodiments, a conduit passes through the projecting portion and the second component. The conduits of the first and second components may be aligned. wherein the projecting portion of the second component deforms an area of the first component surrounding the conduit therein so as to create a seal around the contiguous conduits of the first and second components, thus preventing any fluid from escaping as it flows from one conduit to the other conduit, and wherein the second component is for connecting the conduit therein to an external fluid source or sink.

Some embodiments may include an interconnect system for each of the fluid inlet and fluid outlet. In various embodiments, the interconnect system or systems may include a guide positioned around the conduit on the first component and may mate with the projecting portion of the second component to align the conduits of the first and second components.

In some embodiments, the base of the chamber of a microfluidic device is formed from a substrate for supporting biological material. Some embodiments of substrates may include, but are not limited to glass (e.g., glass slide), plastic, (e.g., polystyrene microscopy slide), culture plate and/or any material known in the art. The chamber may be formed on at least a portion of the substrate. In some embodiments, the substrate may be detachable from the device.

Embodiments of the microfluidic device may be used for culturing cells. 20. In various embodiments, the device may be used for culturing cells and/or performing cell-based assays. Some embodiments may include a housing.

In some embodiments, the fluid inlet and the fluid outlet may be positioned on opposite sides of the chamber. Various embodiments include a fluid inlet and a fluid outlet which are positioned so that a material containment portion of the chamber is substantially unaffected by the flow of fluid through the chamber. In some embodiments, the fluid inlet and/or the fluid outlet each form at least about 20% of the area of one side of the chamber. Embodiments may include a fluid inlet and/or fluid outlet aligned with the top of the chamber. In some embodiments, wherein the fluid inlet and fluid outlet may include one or more flow restrictors.

Embodiments may include a conduit to carry fluid to the fluid inlet and a conduit to carry fluid away from the fluid outlet. Conduits may include one or more flow dividers.

In some embodiments, the sealable port may form a lid of the chamber. Some embodiments may include a liquid as the fluid. In various embodiments, the sealable port may include a gas permeable membrane to allow gas such as oxygen to pass into the chamber.

In some embodiments, the microfluidic device may include a heater and/or sensor.

In some embodiments an interconnect system for sealably connecting two fluid carrying conduits may include a first component having a conduit formed of a deformable material; and a second component having a projecting portion having a conduit which passes through the projecting portion and the first component. In various embodiments, during use, the conduit of the first component is aligned with the conduit of the second component. In some embodiments, when force is applied to the second component the projecting portion deforms an area of the first component surrounding the conduit to create a seal around the contiguous conduits of the first and second components, thus inhibiting and/or preventing any fluid from escaping as it flows from one conduit to the other conduit.

Some embodiments may include an interconnect system configurable to connect and/or connecting a conduit in a microfluidic device to an external fluid carrying conduit.

In some embodiments, the interconnect system may include a guide positioned on the first component around the conduit therein and which mates with the projecting portion of the second component to align the conduit of the first component with the conduit of the second component.

Some embodiments of a microfluidic device may include a chamber having a fluid inlet, a fluid outlet and a substrate for supporting biological material, the fluid inlet and the fluid outlet being positioned to direct fluid flowing from the fluid inlet to the fluid outlet through the chamber. In some embodiments, the substrate forms the base of the chamber of the microfluidic device. Some embodiments of substrates may include, but are not limited to glass (e.g., glass slide), plastic, (e.g., polystyrene microscopy slide), culture plate and/or any material known in the art. The chamber may be formed on at least a portion of the substrate. In some embodiments, the substrate may be detachable from the device.

In some embodiments, a microfluidic device may include an interconnect system having a first component with a conduit to carry fluid to the fluid inlet or away from the fluid outlet. Some embodiments may include a first component formed of a deformable material. Various embodiments may include a second component having a projecting portion and a conduit passing through the projecting portion and the second component. In some embodiments, the conduit of the first component may be aligned with the conduit of the second component, and the projecting portion of the second component may deform an area of the first component surrounding the conduit to create a seal around the contiguous conduits of the first and second components, thus inhibiting and/or preventing any fluid from escaping as it flows from one conduit to the other conduit. In some embodiments, the second component may be used to connect the conduit therein to an external fluid source or sink. The microfluidic device may include an interconnect system for each of the fluid inlet and fluid outlet. Some embodiments may include one or more interconnect systems having a guide positioned on the first component around the conduit which mates with the projecting portion of the second component to align the conduits of the first and components.

In some embodiments, a method of fabricating a microfluidic chip may include forming a mould defining features of the microfluidic chip; pouring a curable polymer into the mould; curing the polymer to form a cured polymer sheet; releasing the cured polymer sheet from the mould; forming a membrane having a base layer and a overlying cured polymer layer; bonding the cured polymer sheet to the membrane; and removing the base layer of the membrane to release the microfluidic chip. Some embodiments may utilize the same curable polymer for pouring the curable polymer into the mould and overlying a cured polymer layer. In various embodiments, the polymer is polydimethylsiloxane (PDMS). Some embodiments may include forming a mould defining features of the microfluidic chip using a milling process. In some embodiments, the PDMS used in pouring polymer into the mould is used in a 10:1 base to curing agent mixture. Some embodiments include clamping a covering sheet on top of the mould prior to the curing process.

In some embodiments, the base layer of the membrane is a silanised silicon wafer and the overlying curable polymer layer is a PDMS layer. Various embodiments may include spin coating the PDMS layer on the silanised wafer at 500 rpm for 50 seconds. In some embodiments, the spin coated PDMS layer may obtain a thickness of substantially 120 micrometres.

In some embodiments, the cured polymer is bonded to the membrane by plasma bonding. In various embodiment, after removing the base layer of the membrane to release the microfluidic chip, a microfluidic chamber is formed in the microfluidic chip. In some embodiments, the PDMS is cured in an oven at about 80° C. for about one hour.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 7A depicts a microfluidic device with the sealable port 51 open. FIG. 7B depicts a microfluidic device with the sealable port 51 closed. Figure C depicts a microfluidic device with the sealable port 51 closed in which the cross section is taken perpendicular to that in FIGS. 7A and 7B.

DETAILED DESCRIPTION OF THE INVENTION

Although the present invention and its advantages have been described in detail, it should be understood that various changes, substitutions and alterations can be made herein without departing from the spirit and scope of the invention as defined in the appended claims.

In some embodiments, a microfluidic device may include a microfluidic perfusion bioreactor and/or a microfluidic chip.

The present invention will now be described by way of example only with reference to the figures.

Figure 1A:
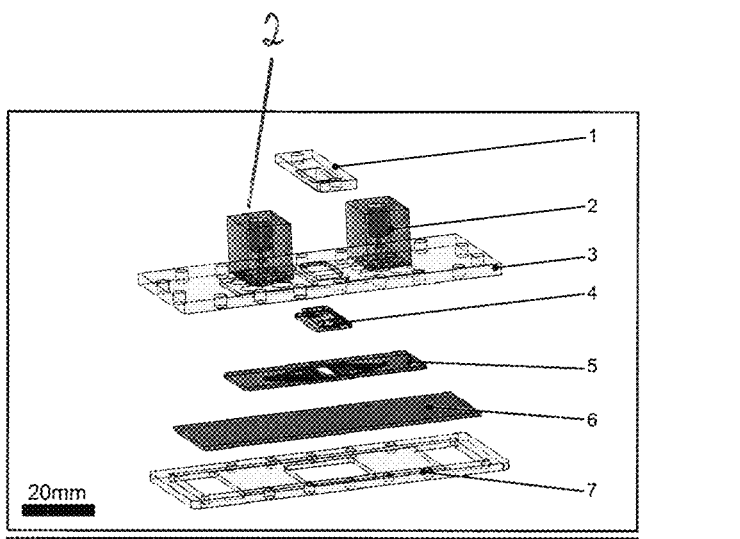
FIG. 1A depicts an exploded view of a microfluidic perfusion bioreactor (MPB).
Figure 1B:
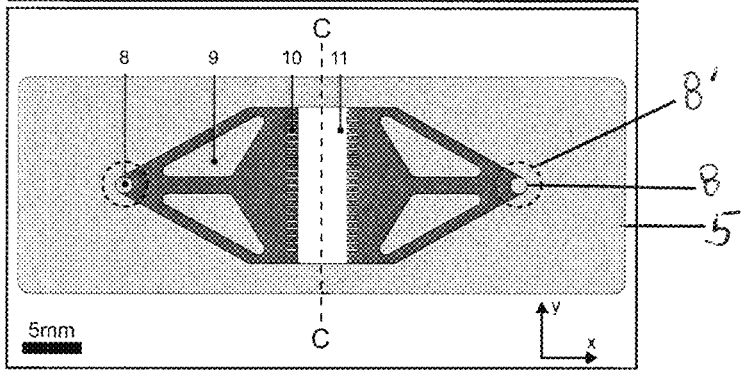
FIG. 1B is a schematic of an embodiment of a microfluidic chip depicting the channel arrangement.
Figure 1C:
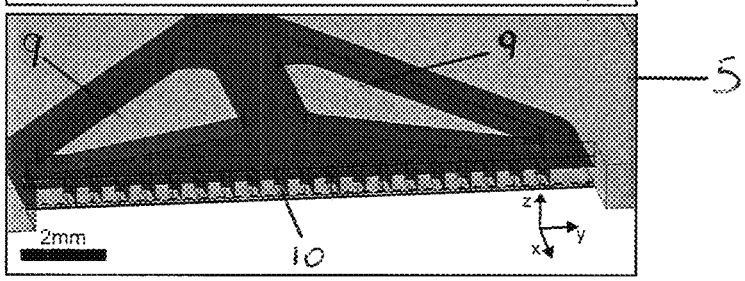
FIG. 1C is a cross-sectional perspective view along line "C" of FIG. 1B depicting a section of a microfluidic chip.

FIG. 1A shows solid models of a microfluidic perfusion bioreactor ("MPB"). FIGS. 1B and 1C depict a microfluidic chip 5. FIG. 1A shows an exploded view of the MPB with its components such as a lid 1, interconnects 2 for tubing, a top plate 3, a gasket 4, a microfluidic chip 5, a cell culture slide 6 and a bottom frame 7. The lid, the top plate and the bottom frame were fabricated in polycarbonate. In some embodiments, any material known in the art may be used to fabricate the lid, top plate and/or the bottom frame. The gasket and the microfluidic chip were made of PDMS. The interconnects were made of aluminium. The cell culture slide was tissue culture polystyrene. FIG. 1B shows a schematic of the channel arrangement of the microfluidic chip with an inlet/outlet port 8, flow dividers 9, flow restrictors 10 and a cell culture chamber body 11 allowing access to the cell culture slide for cell seeding, which has an area of 4 mm×13 mm. The dashed circle around the inlet and outlet port depicts the sealing area 8' of the cylinder of the interconnects. FIG. 1C shows a section in the middle of the microfluidic chip taken through the chamber. The height between the lower solid line and the dashed line depicts the raised inlet channels, whereas the upper solid line approximately depicts the culture chamber height, when the MPB was in perfusion configuration. Some embodiments may include MPBs similar in scale to the devices depicted in FIGS. 1A-1C. In various embodiments, a MPB may vary in size from the scale shown in FIGS. 1A-1C.

Figure 2:
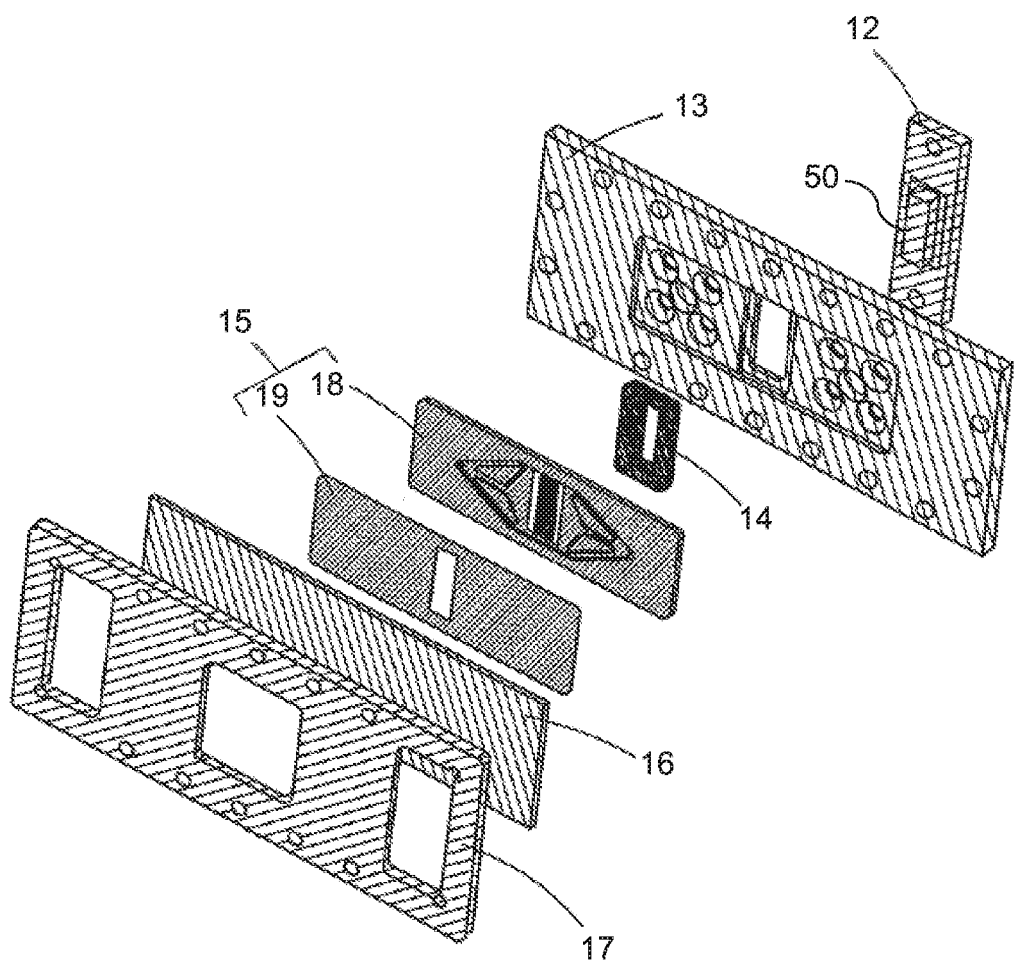
FIG. 2 is an exploded view of an embodiment of a microfluidic perfusion bioreactor (MPB) in a similar manner to FIG. 1A.

FIG. 2 shows an embodiment of solid models of a microfluidic perfusion bioreactor (MPB) similar manner to the MPB depicted in FIG. 1. FIG. 2 shows an exploded view of the MPB with its components such as a lid 12 having a protrusion 50 for sealing the sealable port, interconnects for tubing (shown as 2 in FIG. 1A), a top plate 13, a gasket 14, a microfluidic chip 15 which is formed from two parts: a manifold layer 18; and a membrane 19, a cell culture slide 16 and a bottom frame 17.

Figure 3:
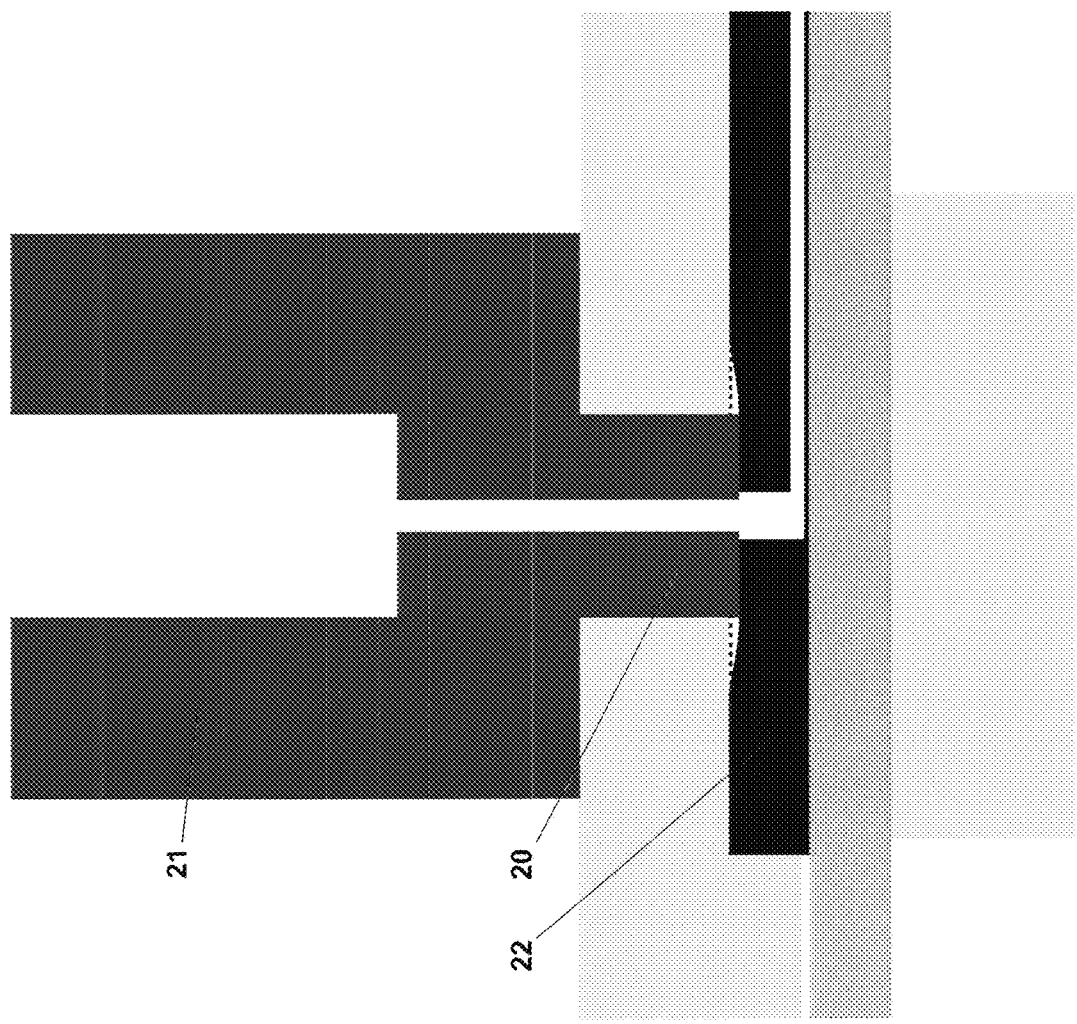
FIG. 3 shows a cross-sectional view of a microfluidic perfusion bioreactor taken along a plane in the interconnect region.

FIG. 3 shows a cross section taken through a MPB in the interconnect region. This figure shows projecting portion 20 on the interconnect 21 pressing into and deforming the microfluidic chip 22 in order to create a seal with microfluidic chip inhibiting and/or preventing leakage. In some embodiments, projecting portion 20 may be a cylinder, nipple and/or any other suitable structure known in the art.

Figure 4:
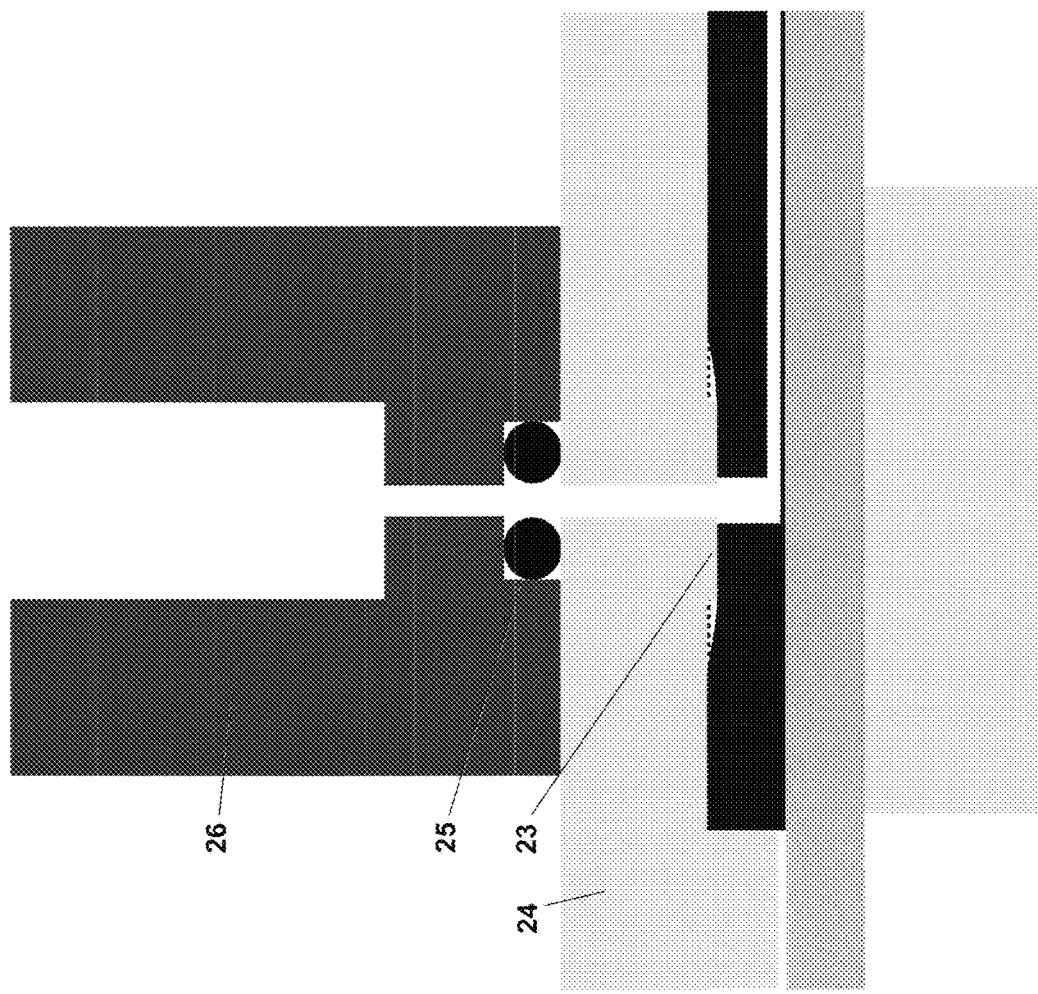
FIG. 4 depicts a cross-sectional view of an alternative embodiment of a microfluidic perfusion bioreactor taken along a plane in the interconnect region.

FIG. 4 shows a cross section of an alternative embodiment of a MPB in the interconnect region. In this embodiment, the projection 23 is on the top plate 24 of the MPB rather than on the interconnect itself. The interconnect 26 is mounted on the top plate and a seal is formed between the top plate and interconnect using a rubberised O-ring 25.

Figure 5:
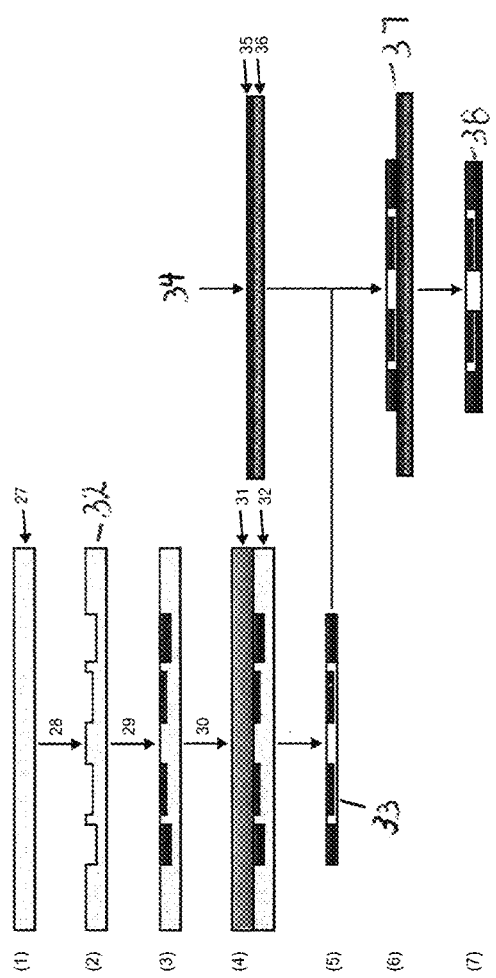
FIG. 5 depicts an embodiment of a fabrication process of a mould and a microfluidic chip created in the mould.

FIG. 5 shows a fabrication process of a mould and a microfluidic chip created in the mould. As shown in step (1) of FIG. 5, sheet 27 may be provided. Sheet 27 may include but is not limited to metals, alloys, such as Dural, and/or any material known in the art. As shown in FIG. 5, in step (2) sheet 27 was machined with a micromilling machine 28 to form a mould 32. In step (3) PDMS was poured 29 into the mould and then degassed. The PDMS was allowed to cure 30. As shown in step (4), a polycarbonate sheet 31 was placed on top of the mould 32 and clamped together. Concurrently, a silanised silicon wafer 36 was spin coated with PDMS 35 to form a membrane 34. The PDMS-coated wafer 34 and the clamped mould were then cured for 1 hour at 80° C. in an oven. Step (5) depicts the microfluidic manifold layer 33 released from the mould and the culture chamber body was cut out. In step (6), the microfluidic manifold layer 33 and the PDMS membrane 34 were exposed to an air plasma and immediately brought into contact for bonding to form structure 37. As shown in step (7). the membrane at the bottom of the culture chamber body was cut out and the microfluidic chip 38 was cut to shape and released from the wafer. In some embodiments, the representations depicted in FIG. 5 are not to scale.

Figure 6:
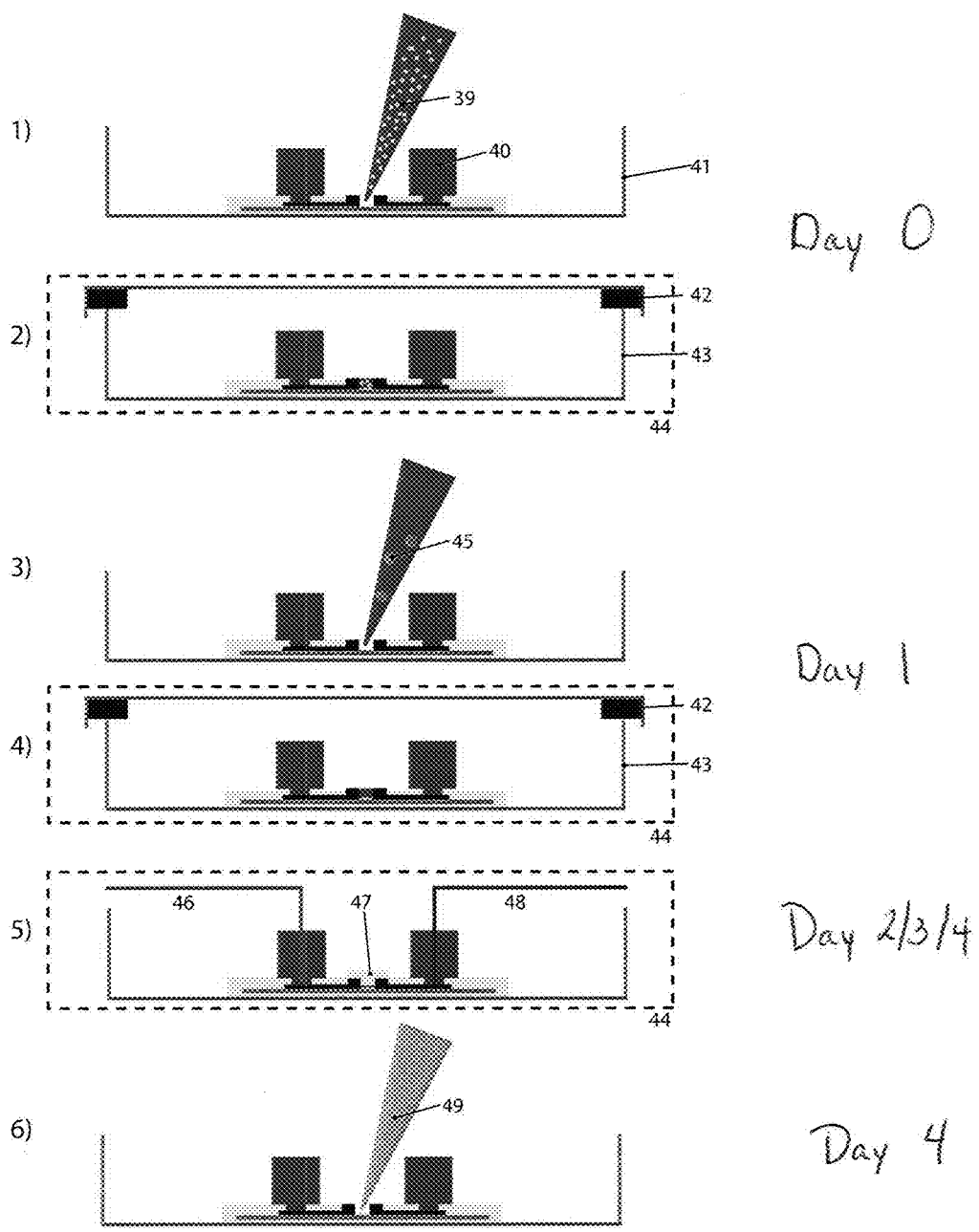
FIG. 6 is a schematic of the procedure for the mircrofusion perfusion bioreactor during seeding and perfusion.

FIG. 6 shows a schematic of the procedure for the MPB in seeding and perfusion configuration. On day 0, MPB 40 and a one well dish 41 were coated with 0.1% gelatine prior to seeding of the feeder layer. As shown in step (1) 20,000 inactivated murine embryonic fibroblasts (MEFs) 39 were seeded with a pipette directly into the cell culture chamber of the MPB and left over night to attach to the surface in an incubator. Step 2 of FIG. 6 depicts Petri dish 43 fitted with spacers 42 for gas exchange used to accommodate the MPB. The Petri dish with the MPB was kept in an incubator at 37° C. and 5% CO2 (b). On day 1, MEF medium was removed and hESC medium added 30 minutes before hESC colonies 45 were seeded. As shown in step (3) hESC colonies 45 were added into the culture area with a pipette (not shown), the Petri dish subsequently closed and the MPB placed back into an incubator 44. On day 2, shown in step (5) medium was aspirated and the culture chamber closed with a lid 47. Tubing 46, 48 was connected to the MPB and perfusion started using a syringe pump for two days in an incubator. On day 4 as shown in step (6), medium was aspirated, cells fixed and stained with pluripotency markers 49 to assess the effect of seeding and perfusion of hESC in a MPB. In some embodiment, dimensions of the various parts shown in FIG. 6 may vary.

Figure 7A:
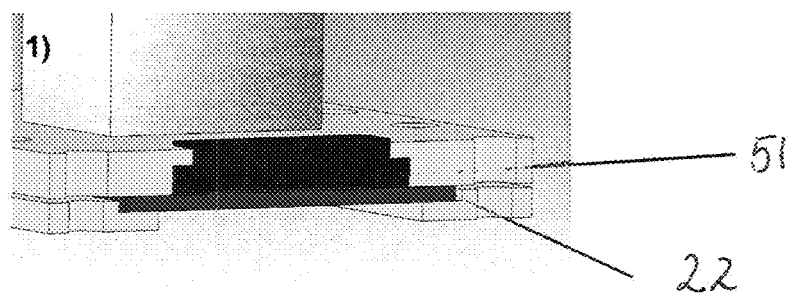
FIGS. 7A-C depict three cross sectional views of a microfluidic device and, in particular, the sealable port.
Figure 7B:
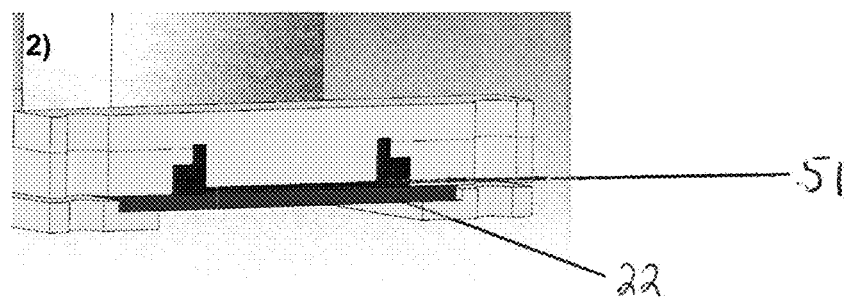
Figure 7C:
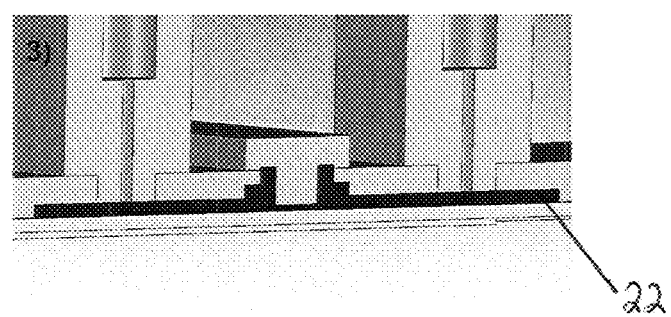

FIGS. 7A-C show three cross sectional views of a microfluidic device and, in particular, the sealable port 51. FIG. 7A depicts a microfluidic device 22 with the sealable port 51 open. FIG. 7B shows a microfluidic device 22 with the sealable port 51 closed. FIG. 7C depicts a microfluidic device 22 with the sealable port 51 closed in which the cross section is taken perpendicular to that of FIGS. 7A and 7B.

In some embodiments, a microfluidic device may include a chamber having a fluid inlet, a fluid outlet and a sealable port. The fluid inlet and the fluid outlet may be positioned to direct fluid flowing from the fluid inlet to the fluid outlet through the chamber. The sealable port may be aligned with the chamber to allow insertion of material into the chamber or extraction of material from the chamber when the sealable port is open, and to inhibit and/or prevent fluid from escaping through the sealable port when the port is sealed.

The sealable port allows material to be placed directly into or removed from the chamber of the device. For example, the sealable port permits easy and gentle seeding of cells and extra-cellular matrix (ECM) compounds into the chamber, the perfusion of the cells and, subsequently, their easy and gentle uptake from the chamber. Alternatively, the port allows the loading and removal of beads or polymer monoliths, for example, for enzymatic assays. The placement of material directly into the chamber and the removal of material from the chamber of the device is done from the exterior of the device, for example, manually using a pipette or other suitable device. This means that the material can be placed directly into the chamber in the precise position that is required for carrying out a particular function. An advantage of the sealable port is that it allows a pre-determined and/or an exact quantity of material to be placed in the chamber which may be crucial for accurately performing assays or tests. Further, this avoids the problems associated with flushing the material into the chamber from an upstream inlet. For example, the problem of high undefined shear stress on the cells as they are flushed into the chamber is avoided. Further, the sealable port may improve the macro-to-micro interface as the port can be opened and closed repeatedly so that different materials can be inserted into and removed from the chamber at will. This provides the device with greater flexibility which enhances the achievable degree of complexity and thus the degree of functionality.

In the context of this invention, the term "microfluidic device" means a miniaturised device through which fluids flow in a controlled manner and in which fluids are geometrically constrained to a small, typically sub-millimeter, scale. Generally, channels in a microfluidic device have dimensions in the order of tens to hundreds of microns and it is through these channels that fluids, normally liquids, flow. A person skilled in the art would appreciate what is meant by this term.

The chamber can be any suitable size and shape so that it can carry out its particular function. For example, in one embodiment, the device is used for culturing cells. Therefore, the chamber is sized so that it can contain a number of cells whilst still allowing fluid to flow through the chamber from the fluid inlet to the fluid outlet in a laminar flow fashion. In such an embodiment, the volume of the chamber may be between about 1 $mm^3$ and about 150 $mm^3$. More preferably, the volume of the chamber will be between about 1 $mm^3$ and about 50 $mm^3$, more preferably still, between about 10 $mm^3$ and about 40 $mm^3$, and most preferably, between about 20 $mm^3$ and about 30 $mm^3$. A suitable chamber might have a length of between about 1 mm and 8 mm, a width of between about 5 mm and about 18 mm and a height of between about 0.2 mm and about 1 mm. A preferred chamber has a length of about 4 mm, a width of about 13 mm and a height of about 0.5 mm. A chamber of this size is particular useful for culturing hESC on a bed of feeder cells. The chamber may be any suitable shape. For example, it may be cuboidal or disc shaped. Preferably, the chamber is cuboidal. Preferably, the chamber has a cross sectional area perpendicular to the flow of fluid of at least about 4 $mm^2$, more preferably, at least about 5 $mm^2$ and, most preferably, at least about 6 $mm^2$. As discussed below, this helps to reduce the flow velocity and shear stress in the chamber.

In some embodiments, the size of the chamber can have an important effect on the conditions inside the chamber. As fluid flows from the fluid inlet to the fluid outlet, the material in the chamber will experience a shear stress as a result of the flow velocity of the fluid around and over the material. Given a constant flowrate, increasing a channel's height and width decreases shear stress as the flow velocity is decreased due to the greater cross sectional area of the channel. Therefore, for the microfluidic device, the larger the chamber dimensions perpendicular to the flow of the fluid, the lower the shear stress that the material in the chamber experiences due to a decreased flow velocity. For cell cultures, the flowrate can be important as it must be high enough to ensure that the cells obtain enough nutrients, such as oxygen, from the medium in order to keep them healthy. By having a chamber with a large area perpendicular to the flow of fluid, it is possible to have a relatively high flowrate but a relatively low flow velocity and, therefore, shear stress. Therefore, the size of the chamber is an important consideration.

The above description relates to the microfluidic device having the sealable port in a sealed position. In one embodiment, the volume defined by the chamber may be greater when the sealable port is not in the sealed position, i.e. when the sealable port is open. This can be achieved by the sealable port having a protrusion which fills part of the volume of the chamber. The advantage of this is that, in certain circumstances, the sealable port can be left in an open position, so that the chamber has a larger volume. For example, when the microfluidic device is used for cell culture, cells can be seeded into the chamber. Having the port open allows more medium to be contained in the chamber, thereby ensuring that the cells are kept in a viable condition. The sealable port can be sealed at a later stage.

In some embodiments, the fluid inlet and the fluid outlet are positioned in such a way so that fluid flowing from the fluid inlet to the fluid outlet may be directed through the chamber. As a result of the fluid flowing through the chamber, material placed in the chamber will come into contact with the fluid as the fluid is passing through the chamber. This ensures that the material is exposed to any substance (e.g. chemicals, reagents, nutrients, enzymes, antibodies, etc.) contained in the fluid. Preferably, the fluid inlet and the fluid outlet are positioned on opposite sides of the chamber. In some embodiments, the fluid inlet and outlet are positioned on the largest face or surface of the chamber. This may ensure that any change in the fluid composition entering the chamber, for example, the introduction of a chemical, is quickly dispersed to the whole chamber and also to any material contained therein. Further, having the inlet and outlet positioned on opposite sides of the chamber may improve or maintain the homogeneity of the flow.

In a preferred embodiment, the fluid inlet and the fluid outlet are positioned so that a material containment portion of the chamber is substantially unaffected by the flow of fluid through the chamber. The material containment portion of the chamber is simply a portion of the chamber which is for containing material which is placed in the chamber. For example, this may simply be the bottom of the chamber. Material placed in the containment portion of the chamber is substantially unaffected by the flow of the fluid in that it is not subjected to a significant shear stress as a result of the flow of the fluid. The flow of fluid is not directed through this containment portion. This is important for cell culture and, in particular, for sensitive cell types like hESC (i.e., human embryonic stem cells). For example, the fluid inlet and the fluid outlet may both be positioned in a top portion of the chamber. In some embodiments, the fluid inlet and fluid outlet are positioned in the top three quarters of the chamber. In this way, material placed in a bottom portion, for example, the bottom quarter of the chamber, is not substantially affected by the flow of fluid as the majority of the flow passes over the top of the material, thus reducing the shear stress that the material experiences. In some embodiments, the fluid inlet and fluid outlet are positioned opposite each other on the side walls of the chamber. Preferably, they are positioned in the top half of the chamber. In various embodiments, the fluid inlet and outlet may be positioned about 120 μm above the base of the chamber. Preferably, the fluid inlet and the fluid outlet are aligned with the top of the chamber. When the material containment portion is at the base of the chamber, the fluid inlet and outlet may be positioned in range from between about 10 μm to about 1 mm above the base of the chamber and, preferably, in a range between about 50 μm to about 300 μm above the base of the chamber. Effectively, this gives a material containment portion having a depth in a range from about 10 μm to about 1 mm and, preferably, having a depth in a range from about 50 μm to about 300 μm.

The reason behind this is that in microfluidic systems fluid flows in a substantially laminar manner. Therefore, material not directly in the path of the flow experiences a much reduced flow velocity and so a much reduced shear stress. Preferably, material placed in the containment portion of the chamber which is substantially unaffected by the flow of fluid experiences a shear stress of less than about 0.001 dyne/cm2 and, more preferably, less than about 0.0001 dyne/cm2.

The fluid inlet and fluid outlet can be any suitable conduit or opening to allow fluid to enter and exit the chamber. A person skilled in the art would be fully aware of standard fluid inlets and fluid outlets used in microfluidics which could be used in the present invention. Preferably, a liquid such as culture medium pass through the chamber from the fluid inlet to the fluid outlet.

The fluid inlet and fluid outlet can be any suitable size or shape. In one embodiment, the fluid inlet, fluid outlet or both are relatively wide or large compared to the chamber. For example, the fluid inlet and/or fluid outlet may have a width which is the same as the width of the chamber. The advantage of having a relatively large fluid inlet and/or outlet is that, for a given flowrate, the flow velocity of the fluid entering the chamber will be relatively low so that the contents of the chamber experience a relatively low shear stress. Preferably, when the chamber is cuboidal, the fluid inlet forms at least about 10% of the area of one side of the chamber. More preferably, the fluid inlet forms at least about 15% of the area of one side of the chamber, more preferably still, at least about 20% and, even more preferably, at least about 30%. Alternatively, the fluid inlet may form between about 10% and about 70% of the area of one side of the chamber, more preferably, between about 15% and about 60% and, even more preferably, between about 20% and about 50%. The fluid outlet and the fluid inlet may be the same size and shape or may be different. The above values and ranges for the size of the fluid inlet are equally applicable to the size of the fluid outlet.

Where the chamber has a curved outer wall, for example where it is disc shaped, the fluid inlet may be positioned anywhere on the curved wall. Where the chamber is cuboidal, that is its outer wall has a number of flat faces joined at the edges of the cuboid, the fluid inlet may be positioned on one of the faces, or over an edge joining two faces. Preferably, it is positioned on one of the faces. Preferably, it is positioned on the widest face. The outlet may be similarly positioned.

The device may have a plurality of fluid inlets and/or fluid outlets. These may be the same size or different sizes. They may carry the same fluid or they may carry fluids with different compositions. If there is a plurality of fluid inlets and/or outlets the above paragraph relating to the area of the chamber side that is formed by the fluid inlet/outlet, relates to the plurality of inlets/outlets, i.e. the fluid inlets preferably form at least about 30% of the area of one side of the chamber, etc.

In one embodiment, a conduit carries fluid to the fluid inlet. Preferably, the conduit increases in cross sectional area as it approaches the fluid inlet. For example, both the height and width of the conduit may increase to form a cone shape. Preferably, the conduit only increases in width as it approaches the fluid inlet. This increase in cross sectional area has the effect of decreasing the fluid velocity in the conduit so that when the fluid enters the chamber through the inlet, the material in the chamber is not subjected to a high shear stress. This is especially the case in microfluidics where the conduit may have dimensions of tens or hundreds of microns. For example, the conduit may increase in width from about 200 μm to about 13 mm where it enters the chamber. Where the conduit increases in width or size, the fluid inlet is preferably positioned on the widest face of the chamber. The fluid outlet can also have a similar feature so that a conduit decreases in cross sectional area as it becomes more distant from the fluid outlet.

In a preferred embodiment, the fluid inlet, the fluid outlet or both comprise one or more flow restrictors. These are thin members which partially obstruct the fluid inlet/outlet so that a plurality of channels are formed in the fluid inlet/outlet and which have the effect of at least partially homogenising the flow velocity of the fluid across the entire width or area of the fluid inlet/outlet. This has the effect of at least partially homogenising the shear stress profile across the chamber. This is especially important where the fluid inlet, fluid outlet or both are relatively wide or large compared to the chamber. Preferably, there is a plurality of flow restrictors. The larger the number of flow restrictors, the more homogenous the flow velocity, and therefore the shear stress profile, will be. Preferably, the flow restrictors are equally spaced in the fluid inlet/outlet so that the channels formed thereby are of equal size. This helps to ensure that the flow velocity is as uniform as possible.

Generally, in mircofluidic devices, fluid is carried to a fluid inlet and away from a fluid outlet in channels or conduits which are of several microns to hundreds of microns in size. In some embodiments, the device may include a conduit to carry fluid to the fluid inlet and a conduit to carry fluid away from the fluid outlet, one or both of the conduits may contain one or more flow dividers. In some embodiments, one or both of the conduits contain a plurality of flow dividers. Flow dividers work in a similar manner to flow restrictors and result in the fluid having a more uniform flow velocity when it reaches the fluid inlet, thus resulting in the fluid having a more uniform flow velocity as it enters the chamber. Preferably, the flow dividers are positioned in the portion of the conduit which increases in size as it approaches the fluid inlet. Similarly, they can be positioned in the decreasing conduits leaving the fluid outlet.

The sealable port is aligned with the chamber to allow insertion of material into the chamber or extraction of material from the chamber when the sealable port is open, and to inhibit and/or prevent fluid escaping through the sealable port when the port is sealed. Preferably, the fluid is liquid. The sealable port can be any suitable size or shape as long as it allows easy insertion and extraction of material into and out of the chamber. The size of the port will depend, in part, on the size of the chamber. The port can be positioned at any suitable point in the chamber. Preferably, the port is in an uppermost portion of the chamber. In one embodiment, the sealable port forms a lid of the chamber so that the uppermost portion of the chamber is formed by the port. The port may be sealed in any suitable way. For example, the port may be sealed using a gasket formed from a deformable material such as rubber or silicone.

In one embodiment in which liquid passes through the chamber, the sealable port comprises a gas permeable membrane to allow gas such as oxygen to pass into the chamber. In this embodiment, when liquid such as culture medium is not flowing through the chamber, oxygen can pass into the chamber so that any cells have the required level of oxygen to keep them healthy. In such an embodiment, the sealable port stops any liquid escaping from (or entering) the chamber but allows gas to pass into the chamber.

In some embodiments of the invention, the chamber, fluid inlet and outlet, and any conduits connected to the fluid inlet and outlet may be encapsulated. For example, they may be encapsulated in a frame or housing. However, in one embodiment, a conduit which connects to the fluid inlet may be made of a gas permeable material, such as PDMS, and at least partially exposed to allow gas to enter the conduit and any liquid contained therein. In such an embodiment, the conduit is for carrying liquid to the fluid inlet. This allows gas such as oxygen to enter the liquid being carried in the conduit so that the gas passes into the chamber with the liquid.

The base of the chamber can be formed from a substrate for supporting biological material. The substrate can be any suitable tissue culture substrate such as glass or polystyrene. Preferably, the substrate is a standard substrate and the chamber is formed on at least a portion of the substrate. For example, suitable standard substrates are glass or polystyrene microscopy slides or culture plates. Suitable culture plates may comprise wells or may not. Preferably, the substrate is detachable from the device. This allows rapid exchange of the substrate or allows the substrate to be removed so that any material on the substrate can be analysed more easily The substrate allows biological material to be attached thereto. For example, cells, antibodies, proteins such as enzymes and ECM compounds can be attached to the substrate.

The fact that the substrate is detachable from the device facilitates the comparison of microfluidic assays with traditional assays, for example, the comparison of traditional cell culturing techniques with microfluidic cell culturing using the same substrate material. Further, the attachment and detachment of the substrate simplifies pre- and post-processing steps which may have to be conducted at another location using conventional larger-scale equipment and which would necessitate the transport of the substrate to and from this other location. The use of a standard substrate, such as a glass or polystyrene microscope slide, makes pre- and post-processing steps much more convenient as the standard substrate can be used directly with conventional larger-scale equipment such as a microscope or plate reader. In one embodiment, the device can be used directly with a microscope so that it is not necessary to detach the substrate to view the biological material attached thereto. This could be done by making the device from transparent material.

The device may include an interconnect system having a first component having a conduit therethrough to carry fluid to the fluid inlet or away from the fluid outlet, wherein the first component is formed of a deformable material, and a second component having a projecting portion, wherein a conduit passes through the projecting portion and the second component. In some embodiments, the conduit of the first component is aligned with the conduit of the second component, and the projecting portion of the second component deforms an area of the first component surrounding the conduit therein so as to create a seal around the contiguous conduits of the first and second components, thus inhibiting and/or preventing any fluid from escaping as it flows from one conduit to the other conduit, and wherein the second component is for connecting the conduit therein to an external fluid source or sink.

Preferably, the device comprises an interconnect system for each of the fluid inlet and fluid outlet.

The advantage of such an interconnect system is that it allows the device to be easily and robustly connected to external fluid sources in a leak-free manner. This vastly improves the macro-to-micro interface. The second component can easily be standardised to allow easy linkage with standard equipment, for example, 'robotised' liquid handling platforms.

The first component is made of a deformable material. This can be any suitable deformable material such as rubber or silicone (e.g. poly(dimethylsiloxane) (PDMS)). The material must be sufficiently deformable to allow the second component to deform it and create a seal therewith.

The second component is for connecting the conduit therein to an external fluid source or sink. This can be any suitable fluid source or sink and can be connected in any suitable way. Such connections are well known to those skilled in the art. For example, the second component can have a thread on the inside of the conduit to allow it to be connected to commonly available tubing connectors such as Upchurch fingertight units. This allows fluid from an external source to enter the device, pass through the chamber and exit the device. The second component can be made of any suitable material. For example, the second component may be made of aluminium.

The projecting portion can be any suitable size or shape so that it can create a seal with the first member to allow fluid to pass from one conduit into the other conduit in a leak free manner. Preferably, the projecting portion is cylindrical in shape so that the conduit passes through the longitudinal axis of the cylinder. A cylindrical shape creates a better seal and it is easier to fabricate.

The conduit in the first and second components can be the same size or different sizes. The cross sectional area of the conduits may change along the length of the components. Preferably, the conduit of the first component has a cross sectional dimension of about 1 mm to about 2 mm. For example, the conduit may have a diameter of about 1 mm to about 2 mm and, more preferably, about 1.2 mm to about 1.4 mm.

Preferably, the interconnect system further comprises a guide positioned on the first component around the conduit therein and which mates with the projecting portion of the second component to align the conduit of the first component with the conduit of the second component. The advantage of the guide is that the two components are self aligning which makes it very easy to correctly connect the two components to align the conduits.

The guide may be any suitable guide for aligning the conduits of the two components. For example, the guide may comprise an opening which is substantially the same size and shape as the projecting portion of the second component so that the projecting portion slots into the guide in a similar manner to a plug and socket.

The microfluidic device may further comprise a heater, such as an electroheater like indium tin oxide, to allow the chamber and its contents to be heated to and maintained at a predetermined temperature. Therefore, when cells are being cultured in the chamber, the chamber can be kept at a suitable temperature rather than being kept in an incubator. Alternatively, the device may comprise a heater to heat the fluid before it reaches the fluid inlet so that fluid entering the chamber has been heated to a predetermined temperature. The heater may be integrated into the device. For example, the heater may be integrated into the substrate of the device in embodiments in which a substrate is present.

The device may further comprise immobilised optical sensors or biosensors. Such sensors, in particular, the optical sensors, could be integrated into the second component of the interconnect system provided they are made of a transparent thermoplastic polymers.

The device may comprise a housing which contains the other elements or to which the other elements are attached. For example, in one embodiment, a microfluidic chip defines the chamber, the fluid inlets and outlets and any conduits connected to the fluid inlet and/or outlet. The housing contains the microfluidic chip and has suitable openings to allow access to the chamber for the sealable port and also to the conduits and/or fluid inlet and outlet. This housing can be a standard size and can accommodates the interconnect systems and the substrate. This can give a standard housing comprising all the necessary elements to provides the macro-to-micro interface for the microfluidic device. Customised microfluidic chips can then be placed in the standard housing according to the particular function of the device allowing easy connection to the sealable port, interconnect system, substrate, etc. In this respect, the housing should allow the device to be assembled and disassembled repeatedly. The housing may be made of any suitable material. For example, the housing may be made of aluminium. Alternatively, the housing may be made of a transparent material.

The present invention also provides an interconnect system for sealably connecting two fluid carrying conduits, the system comprising:

a first component having a conduit therethrough and being formed of a deformable material; and a second component having a projecting portion, wherein a conduit passes through the projecting portion and the first component;

wherein, in use, the conduit of the first component is aligned with the conduit of the second component and a force is applied to the second component so that the projecting portion deforms an area of the first component surrounding the conduit therein so as to create a seal around the contiguous conduits of the first and second components, thus preventing any fluid from escaping as it flows from one conduit to the other conduit.

Preferably, the interconnect system is for connecting a conduit in a microfluidic device to an external fluid carrying conduit.

Preferably, the interconnect system further comprises a guide positioned on the first component around the conduit therein and which mates with the projecting portion of the second component to align the conduit of the first component with the conduit of the second component.

Other features of the interconnect system are as described above.

The present invention also provides a microfluidic device comprising a chamber having a fluid inlet, a fluid outlet and a substrate for supporting biological material, the fluid inlet and the fluid outlet being positioned to direct fluid flowing from the fluid inlet to the fluid outlet through the chamber.

Other features of this device are as described above in relation to the device comprising the sealable port.

The present invention also provides a method of fabricating a microfluidic chip, the method comprising the steps of: a) forming a mould defining features of the microfluidic chip; b) pouring a curable polymer into the mould; c) curing the polymer to form a cured polymer sheet; d) releasing the cured polymer sheet from the mould; e) forming a membrane having a base layer and a overlying cured polymer layer; f) bonding the cured polymer sheet to the membrane; and g) removing the base layer of the membrane to release the microfluidic chip. The same curable polymer can be used in steps b) and e), and can be any suitable polymer such as silicone or polyurethane. Preferably the polymer is polydimethylsiloxane (PDMS). Preferably step a) is carried out by a milling process.

Advantageously, the PDMS in step b) is a 10:1 base to curing agent mixture. In this case, the PDMS is degassed prior to the pouring step. In a preferred embodiment, a covering sheet is clamped on top of the mould prior to the curing process. Preferably, the PDMS is cured in an oven at 80° C. for one hour.

Advantageously, the base layer of the membrane is a silanised silicon wafer and the overlying curable polymer layer is a PDMS layer. The PDMS layer may be spin coated on the silanised wafer at 500 rpm for 50 seconds to obtain a thickness of substantially 120 micrometres. Preferably, the membrane is cured in an oven at 80° C. for one hour.

Conveniently, the cured polymer is bonded to the membrane by plasma bonding.

In a preferred embodiment, a microfluidic chamber is formed in the microfluidic chip following step 7 depicted in FIG. 5.

Where the microfluidic device is used for culturing cells, for example, human embryonic stem cells (hESC), it can be used to study various properties of the cells under different medium perfusion conditions. For example, the impact of oxygen on expansion and differentiation of hESC can be determined. The use of the microfluidic device could also be integrated with post-process cell preparation.

Microfluidic cell culture systems, such as the present invention, operate with significantly fewer resources. They can also be parallelised so that multiple microfluidic devices can be combined into a single system. Further, the use of the microfluidic device can be automated. For example, automated pulse-free medium perfusion of cells can be performed by an automated system for execution of cell re-feed schedules. Alternatively, constant medium perfusion can be performed at different flow rates in a plurality of devices. This is applicable to execute fully-automated differentiation and expansion studies. Further, multiplexing of devices can be used for parallelised execution of cell-based assays.

The present invention will be further illustrated in the following Examples which are given for illustration purposes only and are not intended to limit the invention in any way.

EXAMPLES

Example 1

Design of a Microfluidic Perfusion Bioreactor

As shown in FIG. 1A, to integrate a tissue culture polystyrene slide 6, a standard adherent cell culture material, into a microfluidic perfusion bioreactor, a clamp designed with integrated fluidic interconnects 2 was proposed, where a cell culture slide 6 and a microfluidic chip 5 were disposed between a bottom frame 7 and a top plate 3.

The clamp was held together by screws, where the soft microfluidic chip formed a seal between the culture slide and the interconnects in the top plate. In some embodiments, any fastening mechanism known in the art may be used to hold the MPB together. As shown in FIG. 1A, the top plate 3 included two pockets to hold the gasket 4 and the microfluidic chip 5 and which allowed alignment of the microfluidic chip with the inlet and outlet interconnects 2. Interconnects 2 were mounted on the top plate 3 with screws and a portion of the interconnects extend through a hole in the top plate 3. A projection 20 (shown in FIG. 3) at the bottom of the interconnect was pressed against the microfluidic chip and formed a tight seal 8' (shown as dotted circle in FIG. 1B) around the inlet and outlet port 8 (shown in FIG. 1B), when the MPB was assembled. (shown in FIG. 3)

The projection stood out approximately 80 μm into the microfluidic chip pocket from the top plate to assure that the cylinder is pressed reliably against the microfluidic chip, when clamped.

The interconnects had on the top side a thread, which allowed the use of commonly available tubing connectors, (such as Upchurch fingertight units).

An alternative embodiment of the interconnect is shown in FIG. 4. In this embodiment the projection 23 is on the top plate 24 of the MPB rather than on the interconnect itself. The interconnect 26 is mounted on the top plate and a seal is formed between the top plate and interconnect using a rubberised O-ring 25. Alternatively, the interconnect can be formed integrally with the top plate to allow fabrication of the top plate and interconnect in one piece.

The interconnects can be made of aluminium, thermoplastic polymer and/or other materials known in the art. In some embodiments, aluminium is preferred.

To avoid dissociation of hESC colonies during seeding into the microfluidic perfusion bioreactor, a sealable lid was designed, enabling two configurations of the MPB. When the lid is not mounted, the MPB is in a cell seeding configuration. When the lid is mounted, the MPB is in a perfusion configuration. This allows co-culture seeding and perfusion of hESC on a feeder layer and the use of a pipette for simple and accurate seeding into the MPB (defined colony numbers, cell density).

As depicted in FIG. 1A, a gasket 4 made out of PDMS was incorporated into the design to guarantee a leakage free closing of the MPB after seeding. When the MPB was in seeding configuration, the height of the gasket and the microfluidic chip allowed the same surface area to volume ("SAV") ratio as in a one well dish or a T-flask.

After successful seeding and attachment of the cells, the lid 1 (shown in FIG. 1A) could be screwed onto the top plate 3 to close the MPB. The lid 1 determines the chamber height in the culture chamber during perfusion. In one embodiment, this is about 500 μm (shown in FIG. 1C, upper solid line). This leads to a total volume of about 4 mm×13 mm×0.5 mm=26 microlitres.

As shown in FIG. 1A, this device enables the use of disposable polymeric microfluidic chips 5 which can easily be redesigned and inserted into the standardised housing.

As depicted in FIGS. 1B-C, in some embodiments, the microfluidic chip 5 had nineteen flow restrictors 10 on each side of the cell culture chamber. In various embodiments, the flow restrictors may have dimensions of about 200 μm wide and about 1000 μm long. In some embodiments, channels between the restrictors were about 400 μm wide and about 200 μm high. As shown in FIG. 1b, the inlet 8 was divided into three channels acting as a microfluidic manifold 9 to create together with the flow restrictors 10 an even velocity pattern in the culture area and therefore an even distribution of shear stress within the culture chamber (in flow direction, y-direction).

As shown in FIG. 1C, a layer (shown between lower solid and dashed line) at the bottom of the microfluidic chip elevated the height of the flow restrictors to above the cell culture portion of the chamber (in between the solid line and dashed line at the bottom of the chamber of FIG. 1C), reducing the flow rate and the hydrodynamic shear stress on the cell culture. FIG. 2 depicts the layer as membrane 19.

As shown in FIG. 1B, to accommodate hESC colonies sized up to 1 mm in diameter, an appropriate sized cell culture chamber body 11 was incorporated. In one embodiment of an MPB, the cell culture area had a size of 0.52 $cm^2$.

FIG. 1A depicts bottom frame 7 had a recess incorporated to hold different microscope slide formats. The bottom frame was reinforced underneath the sealing area to avoid excessive bending of the bottom frame when clamped together. An opening under the culture chamber area allowed access for inverted microscopes. The bottom frame was fitted with threads to screw together with the top plate.

Example 2

Fabrication and Assembly of the Microfluidic Bioreactor

All parts and moulds were designed in a 3D CAD system (SolidWorks 2007, Dassault Systemes SolidWorks, USA). G-code was generated with a CAM program (MasterCam X2, CNC Software, USA) to control the milling process on a micro milling machine (M3400E, Folken Industries, USA).

To mill the bottom frame 7 and top plate 3 (shown in FIG. 1A), a 3 mm thick poly(carbonate) (PC) sheet (681-637, RS, UK) was machined (8,000 rpm, 104 mm min$^{-1}$ feedrate) using 2 mm diameter end mills (2 flute standard length, Kyocera Micro Tools, USA). The lid 1 as depicted in FIG. 1A was machined from a 5 mm thick PC sheet (681-659, RS, UK) using 2 mm diameter and 1 mm diameter end mills (2 flute standard length, Kyocera Micro Tools, USA).

Instead of using a SU-8 process, which creates a master for PDMS reproduction, the inventors used a micromilling machine to fabricate moulds for the microfluidic chip (FIG. 5) and the gasket.

As shown in FIG. 5, in steps 1 and 2 the mould 32 for the microfluidic manifold layer was milled 28 (8,000-16,000 rpm, 104 mm min$^{-1}$) in Dural with 2 mm, 1 mm and 200 µm diameter end mills (2 flute standard length, Kyocera Micro Tools, USA). 2 mm and 1 mm diameter end mills were used to create microfluidic manifolds or channels. A 200 µm diameter end mill was used to machine the flow restrictors.

Poly(dimethylsiloxane) (PDMS) (Sylgard 184, Dow Corning, USA) was mixed in a ratio of 10:1, base to curing agent, and degassed for 15 minutes. As shown in step 3 of FIG. 5, the PDMS was poured into the negative Dural mould and thoroughly degassed again until no air bubbles were visible. A 3 mm thick PC sheet was then placed carefully on top of the mould as shown in step 4 of FIG. 5 and clamped between two aluminium plates. The clamped stack was placed in an oven at 80° C. for 1 hour to cure the PDMS.

After releasing the mould/PC sheet stack from the clamping plates, the mould together with the polycarbonate sheet was left to cool. The microfluidic manifold layer was then freed from the mould with tweezers as shown in FIG. 5, step 5. The culture chamber body of the microfluidic manifold layer was cut out with a scalpel under a microscope.

As depicted in FIG. 1C, the thickness of a PDMS membrane defined the height of the flow restrictors above the cell culture chamber (shown as the height between the solid and the dashed line).

First, a 4" silicon wafer (100, P-type, Prolog Semicor, Ukraine) was silanised (85041C, Sigma-Aldrich, UK) to prevent subsequent sticking of the PDMS. 200 µl of the trichlorosilane was pipetted into a vial and placed with the silicon wafer in a desiccator for 1 hour.

5 ml of degassed PDMS was spun with a spin coater (P6708D, Speciality Coating Systems, USA) on the silanised wafer at 500 rpm for 50 seconds to obtain a thickness of approximately 120 µm and placed in an oven at 80° C. for 1 hour.

To bond the thin PDMS membrane 34 with the PDMS microfluidic manifold layer 33, an air plasma was used. Before bonding, the PDMS-coated wafer and the microfluidic manifold layer were rinsed with ethanol and subsequently dried. Both PDMS layers were then exposed to air plasma for 90 seconds at 30 W and 500 mTorr (PDC-002, Harrick Plasma, USA). As shown in step 6 of FIG. 5, the microfluidic manifold layer and the membrane on the wafer were then immediately brought into contact for bonding. To further strengthen the bond, the microfluidic chip 38 was placed in an oven at 80° C. for at least 2 hours.

Step 7 of FIG. 5 depicts cutting the culture chamber body. To provide access to the culture slide, the culture chamber body had to be cut out of the membrane with a scalpel. The microfluidic chip was cut out after and gently released from the silicon wafer with a tweezer.

The interconnect was made of an aluminium block. A thread was cut into the top for an Upchurch fingertight unit. The bottom of the interconnect had a 2.08 mm high cylinder (6 mm in diameter) to form a seal as previously described.

The dimensions of the mould and the microfluidic chip were measured with a stylus profilometer (Dektak 8, Veeco Instruments Company, USA) and the quality of the mould was inspected with a SEM (XB1540 "Cross-Beam", Carl Zeiss AG, Germany).

Prior to assembly, all parts of the MPB were autoclaved, except the cell culture slide. Assembly of the MPB was carried out in a sterile hood.

A sterile tissue culture polystyrene slide (16004, Nunc, Denmark) was placed in the bottom frame. The gasket was placed into the top plate first, followed by the microfluidic chip. The top plate with the microfluidic chip was then carefully placed over the bottom frame with the culture slide and held in place with gently tightened screws, sealing the entire device.

Example 3

Cell Culture Maintenance

Primary murine embryonic fibroblasts (MEF) were maintained in Dulbecco's Modified Eagle Medium (DMEM) (41965, Invitrogen, USA) supplemented with sodium pyruvate (11360, Invitrogen, USA), 10% (v/v) heat inactivated foetal bovine serum (FBS) (10270, Invitrogen, USA) and 1% (v/v) Modified Eagle Medium Non-Essential Amino Acids (MEM NEAA) (11140, Invitrogen, USA) and passaged every 3 days into T75 flasks (159910, Nunc, Denmark) in a humidified environment at 37° C. with 5% CO2.

To inactivate MEFs, the T75 flasks were aspirated and replaced with mitomycin C.

DMEM (11960, Invitrogen, USA) was supplemented with 10% (v/v) FBS (10808, Invitrogen, USA), 1% (v/v) MEM NEAA (11140, Invitrogen, USA) and 8 mg mL-1 mitomycin C (M4287, Sigma-Aldrich, UK) and filtered. 5 mL of mitomycin C solution was added to a T75 flask and incubated for 2 hours at 37° C. The flask was then aspirated and washed with Dulbecco's phosphate buffer solution (DPBS) (D1408, Sigma-Aldrich, UK) three times. Inactivated MEFs were then trypsinized with trypsin:EDTA (T4049, Sigma-Aldrich, UK) and incubated for 3 minutes. The suspension was spun down and the supernatant resuspended. T25 flasks (156367, Nunc, Denmark) were incubated with a 0.1% (v/v) in DPBS gelatine solution (G1890, Sigma-Aldrich, UK) for 10 minutes at room temperature. The flasks were aspirated and filled with 15,000 cells cm-2.

In experiments, the inventors used the Shef-3 cell line obtained from the UK Stem Cell Bank. Use of the line was approved by the UK Steering Committee.

Human ESC (hESC) (Shef-3) were cultivated on a mitomycin-c inactivated feeder layer of primary MEFs (MEFs<passage 5) in T25 flasks (156367, Nunc, Denmark) as stock with filtered KnockOut DMEM (10829, Invitrogen, USA) and KnockOut Serum Replacement (10828, Invitrogen, USA) and supplemented with MEM NEAA (11140, Invitrogen, USA), L-Glutamin (21051, Invitrogen, USA), β-mercaptoethanol (M3148, Sigma-Aldrich, UK) and FGF2 (4114-TC, R & D Systems, USA).

hESC were passaged in small clumps every 3 days using collagenase IV (17104, Invitrogen, USA).

The flasks were incubated with collagenase for 3-5 minutes, before hESC colonies were scraped off the flask surface and replated on a MEF feeder layer.

Example 3

Seeding and Experimental Procedure

The lid of a 150 mm diameter glass Petri dish (2175553, Schott, USA) was fitted with three custom made silicone spacers to enhance gas exchange in an incubator. These Petri dishes were used to provide a sterile environment for the MPB in seeding configuration (FIG. 6).

Prior to seeding, the Petri dishes, pipette tips and tubing to be used were autoclaved and dried.

On day 0, 200 μL of 0.1% (v/v) gelatine in DPBS solution was added into the cell culture area of the MPB and incubated for 10 minutes at room temperature in a sterile laminar flow hood. The gelatine was then aspirated and the MPB was left to dry for 30 minutes. 20,000 inactivated MEFs were seeded into the cell culture area of the MPB (shown in FIG. 6, step 1). The customised lid was put on the Petri dish, which accomodated the MPB, and placed in an incubator (FIG. 6, step 2).

To compare the MPB with traditional static tissue culture methods, three one well dishes (353652, BD Biosciences, USA) were incubated with 0.1% (v/v) gelatine in DPBS solution (G1890, Sigma-Aldrich, UK) for 10 minutes, aspirated and then seeded with 40,000 inactivated MEFs per one well dish.

Inactivated MEFs were counted with a haemacytometer (0630030, Marienfeld, Germany).

Before seeding with hESC colonies on day 1, the one well dishes and the MPB were aspirated and replaced with new hESC medium at least 30 minutes before transferring hESC colonies.

When hESC colonies were routinely passaged in the stock flask, the colonies in medium were transferred into the one well dishes. A drop with hESC colonies in a small Petri dish (Nunc, Denmark) was used to transfer colonies for the MPBs. hESC colonies in the small Petri dish were caught with a 10 μL pipette and then transferred gently to the culture area in the MPB (FIG. 6, step 3) and the Petri dish was closed again (FIG. 6, step 4). One well dishes and MPB were then incubated overnight at 37° C. in an incubator to allow attachment of the hESC colonies to the feeder layer.

On day 2, the hESC colonies had spread and attached to the feeder layer. The medium in the control dishes was replaced every 24 hours for the entire time of the experiment. Medium in the MPB was aspirated, the lid for the MPB put on, tubing for medium and the waste were connected and continuous perfusion was started for 48 hours and was stopped on day 4 of the experiment (FIG. 6, step 5).

The perfusion system consists of a syringe pump (Model 100, KD Scientific, USA), silastic tubing (R3607, Tygon, USA) with Luer adapters (Cole-Palmer, USA), autoclavable tubing (R1230, Upchurch Scientific, USA) with fittings for the custom interconnectors (P207, Upchurch Scientific, USA) and fittings (F331, Upchurch Scientific, USA) for the Luer adapters (P659, Upchurch Scientific, USA), the MPB and a waste bottle. The silicone tubing is gas permeable and equilibriates in an incubator the medium with oxygen while perfusing.

Example 3

Immunocytochemistry

The hESC colonies were characterised by indirect immunochemistry. hESC colonies in control wells and MPB were fixed with 4% (v/v) paraformaldehyde (PDF) in phosphate buffered saline (PBS) for 20 minutes and washed three times in PBS supplemented with 10% (v/v) FBS to block non specific binding (FIG. 6, step 6).

Primary monoclonal antibodies Oct-4 (SC-5279, Santa Cruz, USA), Tra-1-81 (MAB4381, Chemicon, UK) and SSEA-3 (MAB4303, Chemicon, UK) were used at a dilution of 1:200 and incubated with the cells for one hour at 37° C. The cells were then washed three times with PBS and incubated with secondary antibodies with excitation wavelengths of 488 nm (A21212, Invitrogen, USA) and 555 nm (A21426, Invitrogen, USA) for an hour at room temperature. Finally, the cells were stained with DAPI (D1306, Invitrogen, Carlsbad, Calif., USA). DAPI at a dilution of 1:200 was incubated with cells at room temperature for 10 minutes. The MPB and one well dishes were then washed three times with PBS.

In addition, double staining using Tra-1-81 and SSEA-3 antibodies on the same colony was performed.

Example 3

Imaging

For the perfusion experiments and the control wells, we used an inverted microscope (Nikon Eclipse TE2000-U, Nikon Corporation, Japan) with a colour microscope camera (Nikon DS-Fil, Nikon Corporation, Japan) for daily inspection and endpoint assays.

To enhance the immunostaining contrast, the inventors used Photoshop (Photoshop CS3, Adobe Inc., USA).

Results

It was found that the hESC in the MPB were healthy and showed no difference compared to the controls demonstrating that the MPB does not have any detrimental effect on the hESC in any way. This was demonstrated by the fact that the pluripotency of the hESC determined by morphology and immunostaining seemed equal or better than in the static control dish, i.e. the hESC had retained their pluripotency.

Discussion

The above described chip-to-world device offers a robust method of linking a microfluidic chip with the "macroworld". The interface includes a loading port, which can easily and repeatedly be opened and closed. Open, the port permits direct access to a microfluidic chamber. Once closed, the port is leak-free and permits perfusion of said chamber. This sealable port permits easy and gentle seeding of cells and extra-cellular matrix (ECM) compounds into the microfluidic chamber, the perfusion of the cells and, subsequently, their easy and gentle uptake from said chamber. The port also enables the loading and removal of beads or polymer monoliths, for example for enzymatic assays.

Furthermore, the device includes robust and leak-free interconnects for the introduction and collection of solutes (media, drug compounds) into and from the microfluidic chip. The interconnects self-align and seal without the need of O-rings to polymeric microfluidic chips. The location of the interconnects can easily be reconfigured. This ease of reconfiguration enables the microfluidic chip to be specifically designed according to the particular application requirements and independently of chip-to-world design limitations, thereby facilitating rapid prototyping of complete microfluidic devices. Moreover, the device enables the complete encapsulation of a polymeric microfluidic chip in a multi-layer fashion. Again, the device can be opened and closed easily and repeatedly. This multi-layer encapsulation not only enhances the achievable degree of complexity for the microfluidic chip itself (and thus its degree of functionality), but also accepts standard glass microscope slides or polystyrene plates. The use of standard material then facilitates the comparison of microfluidic assays with traditional assays (for example the comparison of traditional cell culturing techniques with microfluidic cell culturing via using the same substrate material). The facile opening and closing of the encapsulation enables the insertion and removal of standard material and thereby simplifies pre- and post-processing steps, which may have to be conducted and transported to and from conventional larger-scale equipment. Finally, the interconnects could potentially be standardised for easy linkage with 'robotised' liquid handling platforms and all materials can be autoclaved, which further broadens the applicability of the device. The described device enables the realisation of microfluidic cell culture systems suitable for drug discovery and drug toxicity testing with minute amounts of cells, tightly controllable environmental conditions, and ease of optical interrogation.

The invention is further described by the following numbered paragraphs:

1. A microfluidic device comprising a chamber having a fluid inlet, a fluid outlet and a sealable port, wherein the fluid inlet and the fluid outlet are positioned to direct fluid flowing from the fluid inlet to the fluid outlet through the chamber, and wherein the sealable port is aligned with the chamber to allow material to be placed directly into, or removed from, the chamber from the exterior of the device when the sealable port is open, and to prevent fluid escaping through the sealable port when the port is sealed.

2. The device of claim 1, further comprising an interconnect system which comprises:
   a first component having a conduit to carry fluid to the fluid inlet or away from the fluid outlet, wherein the first component is formed of a deformable material, and
   a second component having a projecting portion, wherein a conduit passes through the projecting portion and the second component;
   wherein the conduit of the first component is aligned with the conduit of the second component, wherein the projecting portion of the second component deforms an area of the first component surrounding the conduit therein so as to create a seal around the contiguous conduits of the first and second components, thus preventing any fluid from escaping as it flows from one conduit to the other conduit, and wherein the second component is for connecting the conduit therein to an external fluid source or sink.

3. The device of claim 2, comprising an interconnect system for each of the fluid inlet and fluid outlet.

4. The device of claim 2 or claim 3, wherein the interconnect system or systems each further comprises a guide positioned on the first component around the conduit therein and which mates with the projecting portion of the second component to align the conduit of the first component with the conduit of the second component.

5. The device of any preceding claim, wherein the base of the chamber is formed from a substrate for supporting biological material.

6. The device of claim 5, wherein the substrate is a standard glass or polystyrene microscopy slide or culture plate and the chamber is formed on at least a portion of the substrate.

7. The device of claim 5 or claim 6, wherein the substrate is detachable from the device.

8. The device of any preceding claim for culturing cells.

9. The device of any preceding claim, further comprising a housing.

10. The device of any preceding claim, wherein the fluid inlet and the fluid outlet are positioned on opposite sides of the chamber.

11. The device of any preceding claim, wherein the fluid inlet and the fluid outlet are positioned so that a material containment portion of the chamber is substantially unaffected by the flow of fluid through the chamber.

12. The device of any preceding claim, wherein the fluid inlet and/or the fluid outlet each form at least about 20% of the area of one side of the chamber.

13. The device of any preceding claim, wherein the fluid inlet and the fluid outlet are aligned with the top of the chamber.

14. The device of any preceding claim, wherein the fluid inlet and fluid outlet comprise one or more flow restrictors.

15. The device of any preceding claim, further comprising a conduit to carry fluid to the fluid inlet and a conduit to carry fluid away from the fluid outlet, wherein each conduit contains one or more flow dividers.

16. The device of any preceding claim, wherein the sealable port forms a lid of the chamber.

17. The device of any preceding claim, wherein the fluid is a liquid and the sealable port comprises a gas permeable membrane to allow gas such as oxygen to pass into the chamber.

18. The device of any preceding claim, wherein the device further comprises a heater.

19. The device of any preceding claim, wherein the device further comprises a sensor.

20. The use of the device of any one of claims 1 to 19 for culturing cells or performing cell-based assays.

21. An interconnect system for sealably connecting two fluid carrying conduits, the system comprising:
   a first component having a conduit and being formed of a deformable material; and
   a second component having a projecting portion, wherein a conduit passes through the projecting portion and the first component;
   wherein, in use, the conduit of the first component is aligned with the conduit of the second component and a force is applied to the second component so that the projecting portion deforms an area of the first component surrounding the conduit therein so as to create a seal around the contiguous conduits of the first and second components, thus preventing any fluid from escaping as it flows from one conduit to the other conduit.

22. The interconnect system of claim 21, for connecting a conduit in a microfluidic device to an external fluid carrying conduit.

23. The interconnect system of claim 21 or claim 22, wherein the interconnect system further comprises a guide positioned on the first component around the conduit therein and which mates with the projecting portion of the second component to align the conduit of the first component with the conduit of the second component.

24. A microfluidic device comprising a chamber having a fluid inlet, a fluid outlet and a substrate for supporting biological material, the fluid inlet and the fluid outlet being positioned to direct fluid flowing from the fluid inlet to the fluid outlet through the chamber, and wherein the substrate forms the base of the chamber.

25. The device of claim 24, wherein the substrate is a standard glass or polystyrene microscopy slide or culture plate and the chamber is formed on at least a portion of the substrate.

26. The device of claim 24 or claim 25, wherein the substrate is detachable from the device.

27. The device of any one of claims 24 to 26, further comprising an interconnect system which comprises:
   a first component having a conduit therethrough to carry fluid to the fluid inlet or away from the fluid outlet, wherein the first component is formed of a deformable material, and
   a second component having a projecting portion, wherein a conduit passes through the projecting portion and the second component;
      wherein the conduit of the first component is aligned with the conduit of the second component, wherein the projecting portion of the second component deforms an area of the first component surrounding the conduit therein so as to create a seal around the contiguous conduits of the first and second components, thus preventing any fluid from escaping as it flows from one conduit to the other conduit, and wherein the second component is for connecting the conduit therein to an external fluid source or sink.

28. The device of claim 27, comprising an interconnect system for each of the fluid inlet and fluid outlet.

29. The device of claim 27 or claim 28, wherein the interconnect system or systems each further comprises a guide positioned on the first component around the conduit therein and which mates with the projecting portion of the second component to align the conduit of the first component with the conduit of the second component.

30. A method of fabricating a microfluidic chip, the method comprising the steps of:
   a) forming a mould defining features of the microfluidic chip;
   b) pouring a curable polymer into the mould;
   c) curing the polymer to form a cured polymer sheet;
   d) releasing the cured polymer sheet from the mould;
   e) forming a membrane having a base layer and a overlying cured polymer layer;
   f) bonding the cured polymer sheet to the membrane; and
   g) removing the base layer of the membrane to release the microfluidic chip.

31. The method of claim 30, wherein the same curable polymer is used in steps b) and e).

32. The method of claim 30 or claim 31, wherein the polymer is polydimethylsiloxane (PDMS).

33. The method of any one of claims 30 to 32, wherein step a) is carried out by a milling process.

34. The method of any one of claims 30 to 33, wherein the PDMS in step b) is a 10:1 base to curing agent mixture.

35. The method of any one of claims 30 to 34, wherein a covering sheet is clamped on top of the mould prior to the curing process.

36. The method of any one of claims 30 to 35, wherein the base layer of the membrane is a silanised silicon wafer and the overlying curable polymer layer is a PDMS layer.

37. The method of claim 36, wherein the PDMS layer is spin coated on the silanised wafer at 500 rpm for 50 seconds to obtain a thickness of substantially 120 micrometres.

38. The method of any one of claims 30 to 37, wherein the cured polymer is bonded to the membrane by plasma bonding.

39. The method of any one of claims 30 to 38, wherein a microfluidic chamber is formed in the microfluidic chip following step g).

40. The method of any one of claims 30 to 39, wherein the PDMS is cured in an oven at 80° C. for one hour.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

REFERENCES

1. A. Manz, N. Graber and H. M. Widmer, Sens. Actuators B, 1990, 1, 244-248.
2. D. R. Reyes, D. Iossifidis, P. -A. Auroux and A. Manz, Anal. Chem., 2002, 74, 2623-2636.
3. P. -A. Auroux, D. Iossifidis, D. R. Reyes and A. Manz, Anal. Chem., 2002, 74, 2637-2652.
4. S. A. Soper, S. M. Ford, S. Qi, R. L. McCarley, K. Kelly and M. C. Murphy, Anal. Chem., 2000, 72, 642A-651A.
5. T. D. Boone, Z. H. Fan, H. H. Hooper, A. J. Ricco, H. Tan and S. J. Williams, Anal. Chem., 2002, 74, 78A-86A.
6. C. G. Koh, W. Tan, M. Zhao, A. J. Ricco and Z. H. Fan, Anal. Chem., 2003, 75, 4591-4598.
7. E. T. Lagally, C. A. Emrich and R. A. Mathies, Lab Chip, 2001, 1, 102-107.
8. M. A. Burns, B. N. Johnson, S. N. Brahmasandra, K. Handique, J. R. Webster, M. Krishnan, T. S. Sammarco, P. M. Man, D. Jones, D. Heldsinger, C. H. Mastrangelo and D. T. Burke, Science, 1998, 282, 484-487.
9. R. H. Liu, J. Yang, R. Lenigk, J. Bonanno and P. Grodzinski, Anal. Chem., 2004, 76, 1824-1831.
10. A. T. Woolley, D. Hadley, P. Landre, A. J. deMello, R. A. Mathies and M. A. Northrup, Anal. Chem., 1996, 23, 4081-4086.
11. Z. H. Fan, W. Tan, H. Tan, X. C. Qiu and T. D. Boone, Micro Total Analysis Systems, ed. J. M. Ramsey and A. van den Berg, Kluwer Academic Publishers, Netherlands, 2001, pp. 19-21.
12. C. -F. Chou, O. Bakajin, S. W. P. Turner, T. A. J. Duke, S. S. Chan, E. C. Cox, H. G. Craighead and R. H. Austin, Proc. Natl. Acad. Sci. USA, 1999, 96, 13762-13765.
13. N. Goedecke, B. McKenna, S. El-Difrawy, L. Carey, P. Matsudaira and D. Ehrlich, Electrophoresis, 2004, 25, 1678-1686.
14. A. G. Hadd, D. E. Raymond, J. W. Halliwell, S. C. Jacobson and J. M. Ramsey, Anal. Chem., 1997, 69, 3407-3412.
15. G. H. Seong, J. Heo and R. M. Crooks, Anal. Chem., 2003, 75, 3161-3167.
16. D. S. Peterson, T. Rohr, F. Svec and J. M. J. Frechet, Anal. Chem., 2003, 75, 5328-5335.
17. A. E. Herr, J. I. Molho, K. A. Drouvalakis, J. C. Mikkelsen, P. J. Utz, J. G. Santiago and T. W. Kenny, Anal. Chem., 2003, 75, 1180-1187.
18. W. Tan, Z. H. Fan, C. X. Qiu, A. J. Ricco and I. Gibbons, Electrophoresis, 2002, 23, 3638-3645.
19. L. J. Jin, B. C. Giordano and J. P. Landers, Anal. Chem., 2001, 73, 4994-4999.
20. A. Dodge, K. Fluri, E. Verpoorte and N. F. de Rooij, Anal. Chem., 2001, 73, 3400-3409.

21. K. Sato, M. Tokeshi, T. Odake, H. Kimura, T. Ooi, M. Nakao and T. Kitamori, Anal. Chem., 2000, 72, 1144-1147.

22. N. Chiem and D. J. Harrison, Anal. Chem., 1997, 69, 373-378.

23. K. Sato, M. Yamanaka, H. Takahashi, M. Tokeshi, H. Kimura and T. Kitamori, Electrophoresis, 2002, 23, 734-739.

24. J. Moorthy, G. A. Mensing, D. Kim, S. Mohanty, D. T. Eddington, W. H. Tepp, E. A. Johnson and D. J. Beebe, Electrophoresis, 2004, 25, 1705-1713.

25. D. T. Chiu, N. L. Jeon, S. Huang, R. S. Kane, C. J. Wargo, I. S. Choi, D. E. Ingber and G. M. Whitesides, Proc. Natl. Acad. Sci. USA, 2000, 97, 2408-2413.

26. M. G. Roper, J. G. Shackman, G. M. Dahlgren and R. T. Kennedy, Anal. Chem., 2003, 75, 4711-4717.

27. E. Tamaki, K. Sato, M. Tokeshi, K. Sato, M. Aihara and T. Kitamori, Anal. Chem., 2002, 74, 1560-1564.

28. P. C. H. Li and D. J. Harrison, Anal. Chem., 1997, 69, 1564-1568.

29. E. A. Schilling, A. E. Kamholz and P. Yager, Anal. Chem., 2002, 74, 1798-1804.

30. G. Jesson, G. Kylberg and P. Andersson, Micro Total Analysis System' 2003, ed. M. A. Nothrup, K. F. Jensen and D. J. Harrison, 2003, pp. 155-158.

31. V. Nittis, R. Fortt, C. H. Legge and A. J. de Mello, Lab Chip, 2001, 1, 128-152.

32. A. Puntambekar and C. H. Ahn, J. Micromech. Microeng., 2002, 12, 35-40.

33. C. Gonzalez, S. D. Collins and R. L. Smith, Sens. Actuators B, 1998, 49, 40-45.

34. H. Chen, D. Acharya, A. Gajraj and J. -C. Melners, Anal. Chem., 2003, 75, 5287-5291.

35. J. M. Ramsey, Nat. Biotechnol., 1999, 17, 1061-1062.

36. S. Attiya, A. B. Jemere, T. Tang, G. Fitzpatrick, K. Seiler, N. Chiem and D. J. Harrison, Electrophoresis, 2001, 22, 318-327.

37. N. H. Bings, C. Wang, C. D. Skinner, C. L. Colyer, P. Thibault and D. J. Harrison, Anal. Chem., 1999, 71, 3292-3296.

38. Z. Yang and R. Maeda, Electrophoresis, 2002, 23, 3474-3478.

39. Jian Liu, Jian Carl Hansen and R. Quake Stephen, Anal. Chem., 2003, 75, 4718-4723.

40. Khademhosseini A, Langer R, Borenstein J, Vacanti J P. Proc. Natl. Acad. Sci. U.S.A. 2006 Feb. 21; 103(8):2480-7.

41. H. Andersson and A. van den Berg, Lab Chip 4, 98 (2004)

What is claimed is:

1. A microfluidic device for culturing cells comprising: a chamber having a fluid inlet, and a fluid outlet and a sealable port,
    wherein the fluid inlet and the fluid outlet are positioned to direct fluid flowing from the fluid inlet to the fluid outlet through the chamber, and wherein the sealable port is aligned with the chamber to allow cells to be placed directly into, or removed from, the chamber from the exterior of the device when the sealable port is open, and to prevent fluid escaping through the sealable port when the port is sealed: and
    a lid having a protrusion configured to seal the sealable port in a sealed position when the protrusion fills part of a volume of the chamber in a closed position, wherein the chamber has a smaller volume in the sealed position,
    wherein the protrusion is configured to unseal the sealable port in an unsealed position when the protrusion is removed from the part of a volume of the chamber in an open position, wherein the chamber has a larger volume in the open position,
    wherein the protrusion is in contact with the side walls of the chamber when the sealable port is closed,
    wherein the device is operable when the sealable port is open or closed, and wherein the sealable port can be opened or closed during use of the device;
    wherein the chamber is cuboidal,
    wherein the fluid inlet and fluid outlet are positioned on opposite sides of the cuboidal chamber,
    wherein the fluid inlet and the fluid outlet comprise a plurality of flow restrictors that partially obstruct the fluid inlet and fluid outlet to form a plurality of equally sized channels which at least partially homogenize the flow velocity and shear stress profile across the chamber,
    wherein a first conduit carries fluid to the fluid inlet and the first conduit increases in cross sectional area as it approaches the fluid inlet, and a second conduit carries fluid away from the fluid outlet and the second conduit decreases in cross sectional area as it becomes more distant from the fluid outlet,
    wherein each of the first and second conduits comprises a plurality of flow dividers positioned in the portion of the conduit which is changing in cross sectional area, the flow dividers increasing the uniformity of the flow velocity, and
    wherein the base of the chamber is formed from a substrate for supporting biological material.

2. The device of claim 1, wherein the sealable port is configured to be opened or closed with the device remaining operable during use of the device.

3. The device of claim 1, further comprising:
    an interconnect system which comprises:
        a first component having a conduit to carry fluid to the fluid inlet or away from the fluid outlet, wherein the first component is formed of a deformable material, and
        a second component having a projecting portion, wherein a conduit passes through the projecting portion and the second component;
        wherein the conduit of the first component is aligned with the conduit of the second component,
        wherein the projecting portion of the second component deforms an area of the first component surrounding the conduit therein so as to create a seal around the contiguous conduits of the first and second components, thus preventing any fluid from escaping as it flows from one conduit to the other conduit, and
        wherein the second component is for connecting the conduit therein to an external fluid source or sink.

4. The device of claim 3, wherein the device comprises an interconnect system for each of the fluid inlet and fluid outlet.

5. The device of claim 3, wherein the interconnect system or systems each further comprises a guide positioned on the first component around the conduit therein and which mates with the projecting portion of the second component to align the conduit of the first component with the conduit of the second component.

6. The device of claim 1, wherein a base of the chamber is formed from a substrate for supporting biological material, and the chamber is formed on at least a portion of the substrate.

7. The device of claim 6, wherein the substrate is a standard glass or polystyrene microscopy slide or culture plate.

8. The device of claim 6, wherein the substrate is detachable from the device to allow analysis of biological material attached to the substrate.

9. The device of claim 1, wherein a base of the chamber is formed from a substrate for supporting biological material, optionally wherein the substrate is a standard glass or polystyrene microscopy slide or culture plate and the chamber is formed on at least a portion of the substrate, optionally wherein the substrate is detachable from the device to allow analysis of biological material attached to the substrate, such as cells.

10. The device of claim 1, wherein the fluid inlet and the fluid outlet are positioned on opposite sides of the chamber, and the fluid inlet and the fluid outlet are positioned so that a material containment portion of the chamber is substantially unaffected by the flow of fluid through the chamber.

11. The device of claim 1, wherein the fluid inlet and/or the fluid outlet each form at least about 20% of the area of one side of the chamber.

12. The device of claim 1, wherein the fluid inlet and the fluid outlet are aligned with a top of the chamber.

13. The device of claim 1, wherein the fluid inlet and fluid outlet comprise one or more flow restrictors.

14. The device of claim 1, further comprising:
1) a housing;
2) a conduit to carry fluid to the fluid inlet and a conduit to carry fluid away from the fluid outlet, wherein each conduit contains one or more flow dividers;
3) a heater; and/or
4) a sensor.

15. The device of claim 1, wherein the fluid is a liquid and the sealable port comprises a gas permeable membrane to allow gas such as oxygen to pass into the chamber.

16. The device of claim 3 comprising:
a top plate;
a gasket;
a microfluidic chip;
a cell culture slide; and
a bottom frame,
wherein the interconnect system is connected to the top plate,
wherein the microfluidic chip is disposed between the gasket and the cell culture slide, and
the top plate and the bottom frame are assembled to encapsulate the gasket, the microfluidic chip and the cell culture slide.

17. The device of claim 16 wherein, the lid is fitted to the top plate.

18. A method of using the device of claim 1 comprising:
seeding cells in the device when the sealable port is in the open position; and
perfusing the cells when the sealable port is in the closed position.

* * * * *